United States Patent [19]
Ayer

[11] 4,215,702
[45] Aug. 5, 1980

[54] ARTERIAL BLOOD EXTRACTION DEVICE

[76] Inventor: Patrick Ayer, Rte. 3 Woodridge Dr., Eau Claire, Wis. 54701

[21] Appl. No.: 868,971

[22] Filed: Jan. 12, 1978

[51] Int. Cl.² .............................................. A61B 5/14
[52] U.S. Cl. .................................. 128/766; 128/765; 128/771
[58] Field of Search ............. 128/2 F, 2.05 D, 2.05 P, 128/218 NV, 218 P, 218 PA, 234, 276, DIG. 5, 760, 766, 674, 684, 685, 687, 765, 771

[56] References Cited
U.S. PATENT DOCUMENTS

| | | | |
|---|---|---|---|
| 2,866,453 | 12/1958 | Jewett | 128/2.05 D |
| 3,143,109 | 8/1964 | Gewertz | 128/2 F |
| 3,308,809 | 3/1967 | Cohen | 128/2 F |
| 3,310,048 | 3/1967 | Ewing | 128/2 F |
| 3,491,748 | 1/1970 | Pate | 128/2 F |
| 3,730,168 | 5/1973 | McWhorter | 128/2 F |
| 3,886,930 | 6/1975 | Ryan | 128/2 F |
| 3,901,219 | 8/1975 | Kay | 128/2 F |
| 3,942,514 | 3/1976 | Ogle | 128/2 F |
| 3,952,729 | 4/1976 | Libman et al. | 128/2 F |
| 3,993,064 | 11/1976 | McCarthy et al. | 128/218 PA X |

FOREIGN PATENT DOCUMENTS
464109  6/1951  Italy .................................. 128/DIG. 5

*Primary Examiner*—Richard T. Stouffer
*Attorney, Agent, or Firm*—Merchant, Gould, Smith, Edell, Welter & Schmidt

[57] ABSTRACT

A device for the extraction of blood from a vessel and, in particular, for the extraction of arterial blood. The device has structure which permits an immediate visual observation of arterial blood pulsations regardless of the patient's blood pressure once the vessel is punctured. The device includes a container under vacuum and a valve mechanism for regulating the flow of blood into the container. The structure for visual observation of arterial blood pulsations includes a thin-wall conduit with the blood being visible through the wall of the conduit.

11 Claims, 7 Drawing Figures

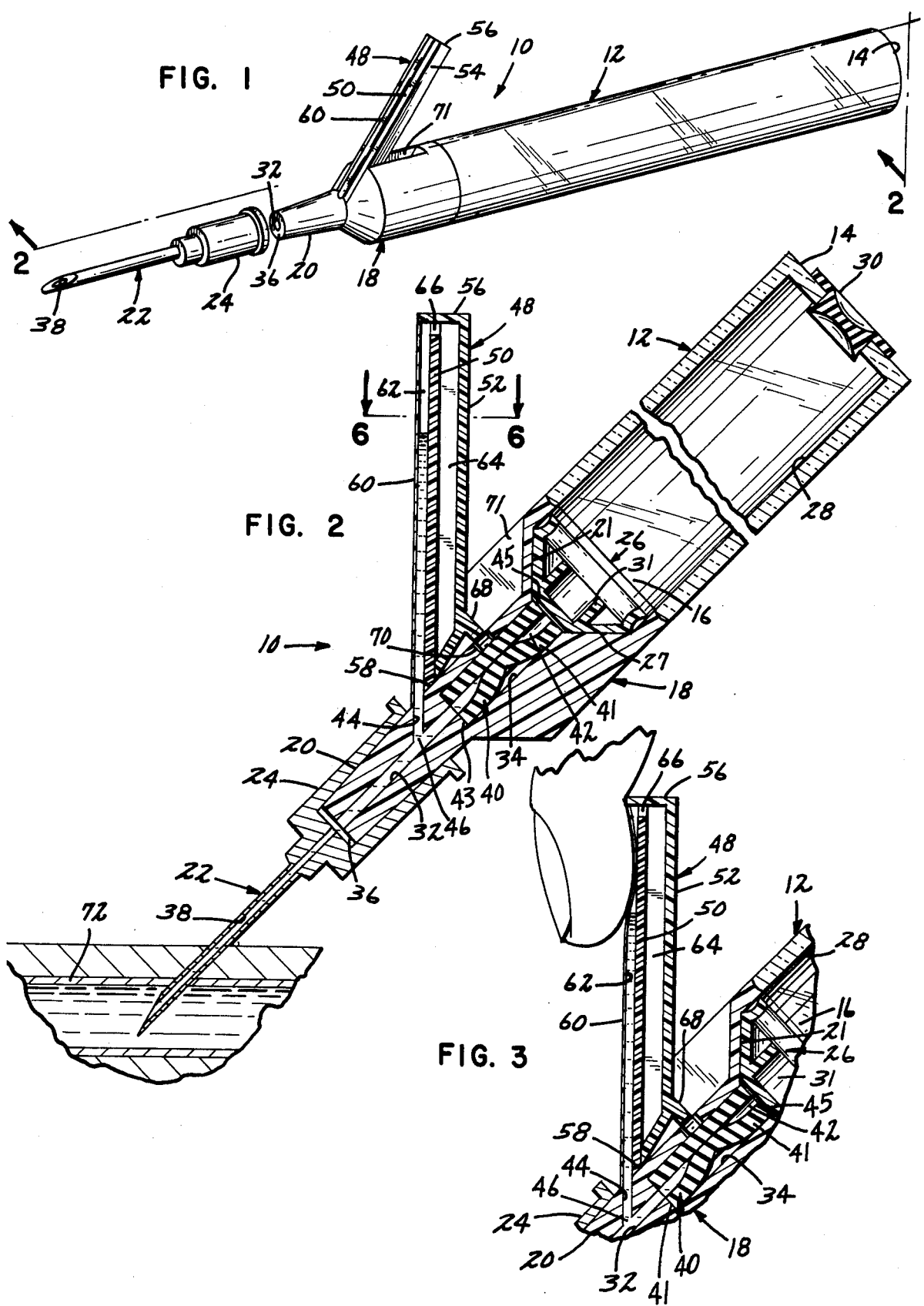
U.S. Patent   Aug. 5, 1980   Sheet 1 of 2   4,215,702

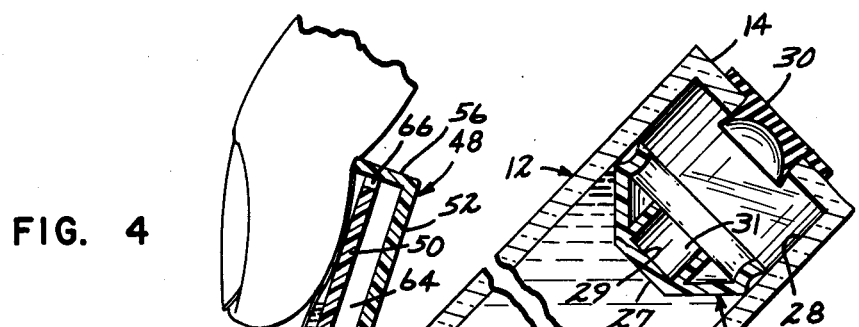
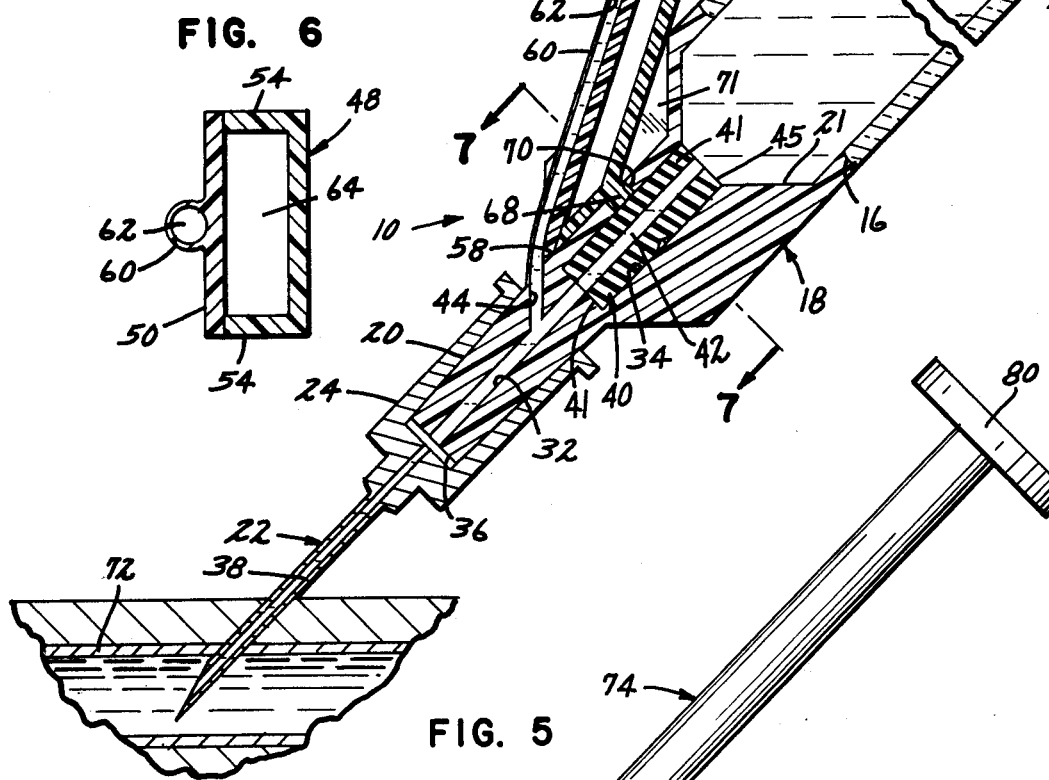
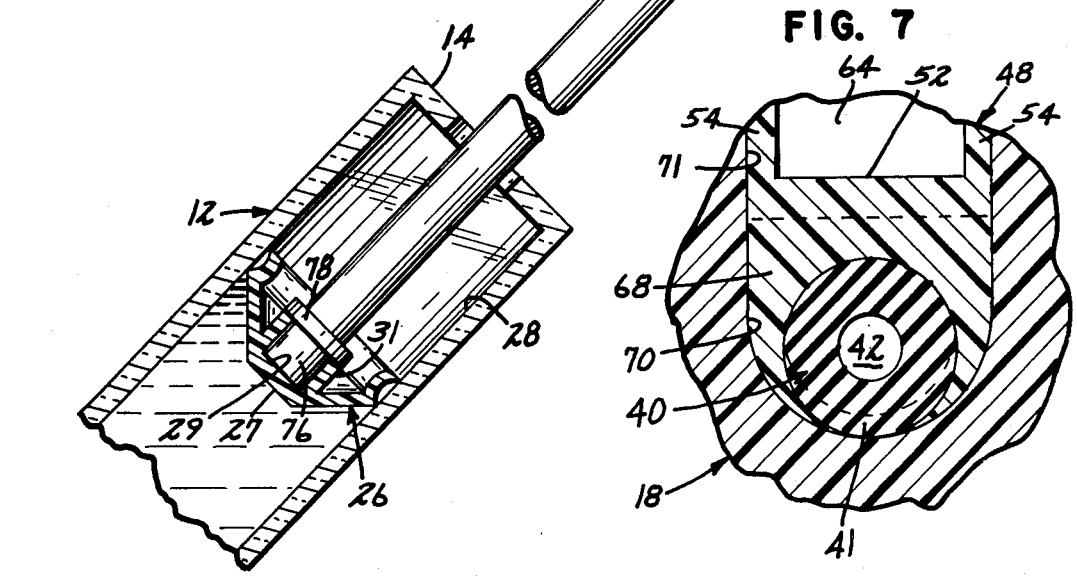

ARTERIAL BLOOD EXTRACTION DEVICE

BACKGROUND OF THE INVENTION

1. Field of the Invention

The present invention relates broadly to a device for extracting blood from a vessel, and, in particular, to a device for the extraction of arterial blood. Arterial blood sampling is recognized as an important diagnostic tool in the treating of patients suffering from lung or heart diseases in particular. In treating these patients, it is important to know the oxygen content of the blood. Oxygen content is determined through blood-gas analysis of arterial blood as opposed to venous blood. In the treatment of such patients, time may be of the essence and it is therefore desirable to have an arterial blood extraction device with which the physician or technician can immediately determine whether or not he is in fact extracting arterial as opposed to venous blood, and additionally such device should not be subject to atmospheric air contamination.

2. Prior Art

In the prior art, two devices and methods are typically utilized to extract arterial blood. One such method utilizes the conventional syringe with integral plunger and needle. The other conventional prior art method utilizes a vacuum container having one end which is punctured by one end of a needle, the other end of the needle being previously inserted into the artery.

With the conventional syringe in order to insure that arterial blood is being extracted, a relatively large size needle, i.e., a 20, 21 or 22 gauge needle, must be utilized. With such larger needles, the pressure of the arterial blood is adequate enough to push the syringe plunger allowing the syringe to fill spontaneously. If a smaller gauge needle, i.e., smaller than 22 gauge, is utilized with a conventional syringe, the blood pressure is inadequate to fill the syringe automatically and the physician or technician must utilize two hands to withdraw the blood. Since the blood does not fill the syringe spontaneously with the smaller needle, there is doubt as to whether or not the blood being extracted is in fact arterial blood. On the other hand, the larger size needles inflict more pain to the patient and it is more difficult to insert the larger size needle into the artery on the first attempt. There is a possibility with the larger size needle of greater damage or trauma to the artery and with the larger size needles part of the needle opening may be within the artery and part may be out of the artery resulting in blood escaping under the skin even while blood is being drawn. The larger size needle generates a larger wound and therefore the compression time to occlude the flow of blood after the extraction procedure is terminated is somewhat long (typically at least five minutes). Finally, an anti-coagulant (heparin) must be mixed with the blood to prevent clotting after the blood is drawn. In liquid form the heparin must initially be drawn into the syringe sufficient to coat the sides of the syringe prior to extracting the arterial blood.

The prior art method utilizing the vacuum tube eliminates the step of drawing liquid anti-coagulant since the interior of the vacuum tube is coated with a thin film of heparin. As previously mentioned, the vacuum tube is utilized in conjunction with a needle which is initially open to the atmosphere at both ends. One end of the needle is placed into the patient's artery. When the physician or technician visually sees blood through the other open end of the needle, the vacuum tube is then pushed over the open end of the needle puncturing the closure at one end of the vacuum tube and permitting the blood to enter the vacuum tube. When the tube is full, the needle must be withdrawn from the artery and a cork rubber stopper is placed over the needle to prevent air from entering the tube which would lead to an erroneous blood-gas analysis. The needle utilized with the vacuum container is typically the larger size needle having similar problems to those discussed above with respect to the syringe method. Additionally, in the vacuum tube method the physician or technician must use two hands to manipulate the tube over the needle to be pushed through the artery as the vacuum tube closure is being punctured. In the vacuum tube method the blood rapidly fills the vacuum tube regardless of whether or not the blood would be arterial or venous. Thus the vacuum tube has a significant problem of proper detection of arterial blood. It should be noted that detection by color is not always accurate. In the case of a patient having a low oxygen content in the blood the arterial blood will appear as very dark colored and similar to the color of venous blood in a person with a normal oxygen content. Vital time may be wasted if a blood sample is sent to the lab for analysis and the results indicate that the blood is venous blood. The treatment of acutely ill patients often depends on rapid and accurate determination of arterial blood-gas values. A delay of several minutes, which may not be uncommon in the prior art arterial blood extraction devices and methods may be critical to proper treatment.

Both prior art devices may be subject to air contamination during the extraction procedure. At times during the procedure the blood flow may stop indicating that the needle has somehow come out of the artery. The physician or technician must therefore probe in an attempt to reenter the artery. If during this attempt to reenter the artery, a portion of the needle bevel or opening comes out of the skin, air may enter the blood already extracted contaminating the blood and creating an erroneous blood-gas analysis.

The present invention overcomes the disadvantages of the prior art devices and methods in that it is an arterial blood extraction device which provides an immediate visual confirmation of arterial blood and which is adapted for use with a small size needle, i.e., 25 guage, that facilitates ease of entry into the artery and minimizes trauma to the artery and pain experienced by the patient. In the device of the present invention arterial blood is detected visually regardless of whether or not the patient has high or low arterial blood pressure. In the present device blood extraction can be terminated at any time during the procedure with the extracted blood sealed and thus not subject to air contamination. The arterial blood extraction device of the present invention can also be manipulated utilizing one hand thereby minimizing any movement of the needle once the needle is in position within the artery. Although the device of the present invention is designed in particular for arterial blood extraction it is to be understood that the device can also be utilized for venous blood extraction.

SUMMARY OF THE INVENTION

The present invention is a device for extracting blood from a vessel and includes a container member under vacuum. The container member has an open end and a closed end, and a valve body member is affixed to the open end of the container member. The valve body member has a second end which is sized to receive a cannula or needle. The valve body portion has an axial passageway therethrough which provides fluid communication between the cannula and the container member. The valve means is affixed to the valve body member to regulate the flow of blood through the axial passageway. The valve means is adjustable to any position between fully open in which the axial passageway is unrestricted and fully closed wherein the axial passageway is blocked. Valve means is normally biased toward a position wherein the axial passageway is fully closed. The present invention further includes a means for visually detecting arterial blood pulsations. In the preferred embodiment, the valve means in the present invention includes a tubular member disposed within the valve body member and having an axial passageway therethrough which defines a portion of the axial passageway through the valve body member. The tubular member has first and second ends and a continuous flexible side wall therebetween. Means are provided for selectively pinching the flexible side wall upon itself transverse to the axis of the tubular member and the pinching means is further biased to a first position in which the second axial passageway is closed thereby blocking fluid communication between the cannula and the container member. The pinching means includes a lever arm affixed to the valve body member and mounted for pivotal movement between a first position wherein the axial passageway through the tubular member is closed and a second position wherein the axial passageway through the tubular member is open. The lever arm has a pinching member extending therefrom which is received within a recess in the valve body member and which is provided with an aperture in which the tubular member is mounted. The recess is disposed generally transverse to the central axis of the tubular member and means are provided for biasing the lever arm toward the first position such that the side wall of the tubular member is collapsed upon itself. The visual detection means includes a thin-wall conduit member affixed to the lever arm. The lever arm has front, rear, end and side walls which define an enclosed air chamber. An aperture is provided in the front wall of the lever arm and one end of the thin-wall conduit opens into the aperture providing fluid communication between the conduit and the enclosed air chamber. The opposite end of the thin-wall conduit member is in fluid communication with the axial passageway through the valve body member at a point between the cannula and the tubular member.

In operation, when the cannula is inserted into the artery, blood will be visible in the thin-wall conduit while fluid communication through the axial passageway to the container member is blocked. The rise and fall of the blood within the thin-wall conduit member provides an indication that an artery as opposed to a vein has been in fact punctured. Such visible pulsation will be present regardless of blood pressure and utilizing a small size needle (i.e., 25 gauge). Once the physician or technician has assured himself that an artery has in fact been punctured, he simply depresses the lever opening the axial passageway through the tubular member and the container member will spontaneously fill with arterial blood under the suction of the vacuum within the container member. At any time during the procedure blood extraction can be terminated simply by releasing the lever whereby the lever arm returns to its biased first position closing the axial passageway through the tubular member.

The present invention thus eliminates the disadvantages of the prior art devices and methods in that it provides a device that gives an accurate indication to whether or not an artery has been punctured and additionally is a device that substantially eliminates the problems associated with contamination from atmospheric oxygen that is not uncommon in the conventional prior art devices and methods. These and other advantages of my invention will become apparent with reference to the accompanying drawings, detailed description of the preferred embodiment, and claims.

BRIEF DESCRIPTION OF THE DRAWINGS

FIG. 1 is a view in perspective of the blood extraction device of the present invention;

FIG. 2 is a sectional view taken generally along the liens of 2—2 of FIG. 1 and illustrating the present invention inserted into a blood vessel and prior to extraction of blood from the vessel;

FIG. 3 is a fragmentary sectional view of a portion of FIG. 2;

FIG. 4 is a sectional view taken along the line 2—2 of FIG. 1 illustrating the present invention while blood is being extracted from the artery;

FIG. 5 is a fragmentary sectional view showing the insertion of a plunger to expel the extracted blood from the device;

FIG. 6 is a partial view in section taken generally along the line 6—6 of FIG. 2;

FIG. 7 is a sectional view taken generally along the line 7—7 of FIG. 4;

DETAILED DESCRIPTION OF THE PREFERRED EMBODIMENT

Referring to the drawings, wherein like numerals represent like parts throughout the several views, FIG. 1 is a view in perspective of the arterial blood extraction device of the present invention designated generally as 10. Device 10 includes a container member 12 which is typically a cylindrical glass member having a closed end 14 and an open end at 16. A valve body member 18 is affixed to container member 12 at open end 16. Valve body member 18 is typically molded of a suitable plastic material and may be adhered to container member 12 in any convenient manner. Valve body member 18 has a tapered end portion 20 sized to receive a cannula or needle 22. Needle 22 has a hub 24 which is secured to tapered end portion 20.

As shown in more detail in FIG. 2, a free floating piston 26 is received within container member 12. Piston 26 is mounted for reciprocating movement along a generally longitudinal central axis of container member 12. Piston 26 engages an inner side wall 28 of container member 12 so that piston 26 is guided in its reciprocal movements. The interior of container member 12 is typically under vacuum and piston 26 is disposed proximate open end 16 and in engagement with valve body member 18 prior to insertion of needle 22 into a blood vessel. Inner side wall 28 is generally coated with a thin film of anti-coagulant substance to prevent the extracted blood from clotting within container member 12. Typically, the anti-coagulant utilized to coat side wall 28 is heparin. Closed end 14 of container member 12 is provided with an aperture in which is placed a closure member 30. Closure member 30 may be formed of a suitable resilient material, such as rubber. Closure member 30 serves dual purposes which will be described in more detail hereafter.

Valve body member 18 has a central axial passageway therethrough that includes a first portion 32 and a second portion 34. The axial passageway defined by first portion 32 and second portion 34 provides fluid communication between an outer end 36 of tapered end portion 20 and the interior of container member 12. Needle 22 also includes an axial passageway 38 which is aligned with the axial passageway within valve body member 18 when needle 22 is affixed to tapered end portion 20. Second portion 34 of / the axial passageway within valve body member 18 has an inside diameter that is greater than the inside diameter of first portion 32. A tubular conduit member 40 is received within second portion 34. Tubular member 40 has a continuous sidewall 41 between a first end 43 and a second end 45 thereof and is formed of a flexible material, i.e., rubber, with an outside diameter substantially equivalent to the inside diameter of second portion 34 of the axial passageway through valve body member 18. Tubular member 40 has an axial passageway 42 therein which is aligned with first portion 32 of the axial passageway within valve body member 18 and which has a cross-sectional flow area substantially equivalent to the cross-sectional flow area of first portion 32. As will be described in more detail hereafter, tubular member 40 may be pinched together to occlude or block fluid communication between first portion 32 and the interior of container member 12.

A second fluid passageway 44 is provided in tapered end portion 20 and intersects first portion 32 of the axial passageway through valve body member 18 at a point 46 disposed between outer end 36 and second portion 34. Passageway 44 intersects first portion 32 preferably at an angle of 45° with respect to the central axis of the axial passageway through valve body member 18. A lever 48 includes a top wall 50, a bottom wall 52, a pair of oppositely disposed side walls as indicated at 54, and and end wall 56. Lever 48 is affixed at point 58 to valve body member 18. Lever 48 is also preferably formed of a suitable plastic material and in the preferred embodiment is molded integrally with valve body member 18. It will be understood, however, that lever 48 and valve body member 18 may be separately manufactured. Lever 48 has limited pivotal movement about point 58 from a first position as shown in FIG. 2 to a second position as shown in FIG. 4. The connection at pivot point 58 is such that lever 48 is normally biased for the position shown in FIG. 2 by the inherent elastomeric properties of the plastic material utilized in the manufacture of lever 48 and valve body member 18 or by a suitable biasing means in the event that lever 48 and valve body member 18 are separately manufactured elements. Affixed to top wall 50 of lever 48 is a thin-wall conduit member 60 that is generally circular in cross section. Conduit member 60 defines a fluid passageway 62 which is in fluid communication with second passageway 44 and tapered end portion 20. Conduit member 60 is preferably thin enough so that fluid within passageway 62 can be visually observed. Top wall 50, back wall 52, side walls 54 and end wall 56 define an enclosed air chamber 64. An opening is provided at 66 between top wall 50 and end wall 56 connecting fluid passageway 62 with enclosed air chamber 64.

Projecting from bottom wall 52 of lever 48 in a direction generally transverse to the central axis of axial passageway through valve body member 18 is a valve member 68. Valve member 68 is received for reciprocal movement within a slot 70 formed within valve body member 18. Slot 70 intersects second portion 34 of the axial passageway through valve body member 18. As shown in more detail in FIG. 7, valve member 68 has an aperture therein in which is received tubular conduit member 40. With lever 48 in a position shown in FIG. 2, valve member 68 causes the lower portion of the side wall of tubular member 40 to collapse upon the upper portion of the side wall of tubular member 40 thereby closing or occluding axial passageway 42. When lever 48 is pivoted against the inherent elastomeric biasing force about point 58 to the position illustrated in FIG. 4, tubular conduit member 40 assumes a relaxed or unstressed state wherein axial passageway 42 is open providing fluid communication between first portion 32 of the axial passageway through valve body member 18 and container member 12. It should be noted that valve body member 18 is provided with an elongated recess or channel at 71 to permit the movement of lever 48 about pivot point 58.

The operation of the present invention will now be described with particular reference to FIGS. 2–6. Device 10 is inserted into an artery 72 or other blood vessel with the needle at an approximately 45° angle with respect to the skin surface. Needle 22 is preferably a small needle, on the order of a 25 gauge needle, which provides an easier entry into the artery in addition to less trauma to the artery. Also the patient will experience less pain with a smaller gauge needle. As illustrated in FIG. 2, when needle 22 is first inserted into the artery, lever 48 is biased such that axial passageway 42 is blocked. The arterial blood enters first portion 32 of the axial passageway in valve body member 18, second passageway 44, and fluid passageway 62. Enclosed air chamber 64 provides a pressure head above the blood in passageway 62 preventing the blood from spilling into chamber 64. The arterial blood within thin-wall conduit member 60 will rise and fall in conjunction with the patient's pulse regardless of the patient's blood pressure. These blood pulsations will be visible through thin-wall conduit member 60 such that the attending physician or technician is assured that an artery has been punctured. Device 10 can be calibrated so that by merely observing the high and low points of the blood pulsations within fluid passageway 62 the patient's blood pressure can be read. When needle 22 is inserted at the proper 45° angle with respect to the skin, fluid passageway 62 will generally be oriented vertically or normal with respect to the skin surface.

Once the physician or technician is assured that an artery has been punctured, he will then begin the process of extracting the arterial blood. Initially, a finger is placed against the exterior surface of thin-wall conduit member 60 to flatten thin-wall conduit 60 against top wall 50. This step is illustrated in particular in FIG. 3. It will be noted that the pressure initially applied against lever 48 is sufficient to collapse thin-wall conduit member 60 thereby preventing reverse flow of blood within fluid passageway 62 once axial passageway 42 is opened, while at the same time the initially applied pressure is insufficient to rotate lever 48 about point 58. The continued application of downward pressure against lever 48 will gradually release the pinching engagment of valve member 68 on tubular conduit member 40. Thus, the vacuum within container member 12 may gradually be applied through axial passageway 42. The arterial blood will begin to flow into container member 12 under the application of the vacuum therein driving free floating piston 26 toward closed end 14. As shown in FIG. 4 and FIG. 7, lever 48 has been depressed such that axial passageway 42 is completely open and container member 12 is substantially filled with arterial blood. Since the suction of the vacuum within container member 12 can gradually be applied through tubular conduit member 40 the chances of an arterial wall being pulled over the opening of needle 22 is significantly reduced. Additionally, during the course of the procedure if it becomes necessary to terminate blood extraction, lever 48 is simply released whereby lever 48 will return to the position shown in FIG. 2 under the biasing force inherent in the elastomeric characteristics of the plastic material of which lever 48 and valve body member 18 are formed. Thus, if needle 22 must be removed from the artery for any reason, there is no chance that the arterial blood within container member 12 would become contaminated with atmospheric oxygen since axial passageway 42 will be closed. After any problems have been resolved, needle 22 can again be inserted into artery 72 and lever 48 depressed to complete the arterial blood extraction.

Closure member 30 can be removed for the insertion of a plunger 74 to expel the extracted blood from container member 12 into a test machine (not shown). Free-floating piston 26 is a generally frusto-conical member having a front surface 27 and a rear surface 29 to which is affixed a socket 31 in which is received an end 76 of plunger 74. Valve body member 18 has a generally conical surface 21 which engages front surface 27 of free floating piston 26 when free floating piston 26 is disposed in the position illustrated in FIG. 2. Plunger 74 is provided with a flange 78 to facilitate the engagement of end 76 within socket 31. Plunger 74 has a disc-shaped member 80 which is depressed by the technician to expel the arterial blood from container member 12. Closure member 30 performs an additional function of providing a visual indication of the maintenance of proper vacuum within a container member 12. In particular, with a proper vacuum within container member 12, closure member 30 will have a generally concave external surface. If the vacuum within container member 12 is inadequate, the outer surface of closure member 30 may be flat or slightly bowed outward.

It should be noted that during the procedure of arterial blood extraction, the physician or technician may manipulate device 10 with a single hand. Device 10 is completely inserted into the artery with a single puncture requiring no subsequent movement of the needle once the needle is in the artery thereby eliminating problems that occur in the prior art conventional syringe and vacuum container methods wherein the possibility exists of the needle being pulled out of the artery during blood extraction or being driven completely through the artery wall as a result of additional required manipulations. Device 10 also provides a visual indication that an artery has in fact been punctured through visible blood pulsations regardless of arterial blood pressure. Blood extraction can be regulated and adjusted manually through lever 48 which controls the opening or closing of axial passageway 42. Unlike the prior art devices and methods, the procedure can in fact be terminated and subsequently resumed with no chance of atmospheric air contaminating the extracted blood. Finally, in keeping with the modern trend in medical devices, the device of the present invention is relatively easy to manufacture at low cost and is therefore a conveniently disposable device.

What is claimed is:

1. A device for extracting blood from a vessel utilizing a cannula or needle, comprising:
    (a) a container member under vacuum having a closed and an open end;
    (b) a valve body member having a first end affixed to said open end of said container member and a second end sized to receive the cannula, said valve body member having a first axial passageway therethrough providing fluid communication between the cannula and said container member, and a recess intersecting said first axial passageway and aligned generally transverse with respect to the axis of said first axial passageway; and
    (c) valve means affixed to said valve body member for regulating the flow of blood through said axial passageway, said valve means including a tubular member having first and second ends and a continuous flexible side wall therebetween defining a second axial passageway, said second axial passageway defining a portion of said first axial passageway through said valve body member and means for selectively pinching said flexible side wall upon itself transverse to said second axial passageway, said pinching means normally biased to a first position wherein said flexible side wall is pinched upon itself completely closing said second axial passageway, said pinching means comprising:
        (i) a lever arm affixed to said valve body member and mounted for pivotal movement between said first position wherein said axial passageway is completely closed and a second position wherein said axial passageway is fully open;
        (ii) a pinching member affixed to said lever arm and mounted for reciprocal movement within said recess, said pinching member having an aperture therein in which is received said tubular member, said pinching member in said first position collapsing said side wall of said tubular member upon itself, said pinching member in said second position permitting said tubular member to regain its tubular shape so that said axial passageway is fully open.

2. A device for extracting blood from a vessel utilizing a cannula or needle, comprising:
    (a) a container member under vacuum having a closed end with a removable closure member and an open end;
    (b) a valve body member having a first end affixed to said open end of said container member and a second end sized to receive the cannula, said valve body member having a first axial passageway therethrough providing fluid communication between the cannula and said container member;
    (c) valve means affixed to said valve body member for regulating the flow of blood through said axil passageway, said valve means adjustable to any position between fully open wherein said axial passageway is unrestricted and fully closed wherein said axial passageway is blocked, said valve means normally biased toward a first position wherein said axial passageway is blocked;
    (d) a free floating piston mounted for reciprocal movement within said container member, said piston disposed proximate said open end of said container member prior to beginning blood extraction; and
    (e) plunger means sized to engage said free floating piston for driving said piston toward said open end of said container member whereby extracted blood may be expelled from said container member.

3. A device for extracting arterial blood utilizing a cannula or needle comprising:
   (a) a container member under vacuum and having a closed end and an open end;
   (b) a valve body member having a first end affixed to said open end of said container member and a second end sized to receive the cannula, said valve body member having a first axial passageway therethrough providing fluid communication between the cannula and said container member;
   (c) valve means affixed to said valve body member for regulating the flow of blood through said first axial passageway, said valve means normally biased to a first position wherein said first axial passageway is closed, said valve means including
      (i) a lever arm affixed to said valve body member and mounted for pivotal movement between said first and a second position wherein said axial passageway is open;
      (ii) constriction means affixed to said lever arm for selectively constricting flow through said axial passageway, said constriction means in said first lever arm position completely closing said axial passageway and said constriction means in said second lever arm position fully opening said axial passageway; and
      (iii) resilient means for biasing said lever arm toward said first position; and
   (d) means for visually detecting arterial blood pulsations regardless of arterial blood pressure prior to selectively opening said axial passageway by moving said lever arm to said second position.

4. A device in accordance with claim 3 wherein said visual detection means further comprises:
   (a) a thin-wall conduit member having a first end in fluid communication with said first axial passageway between the cannula and said valve means, and a second end; and
   (b) a chamber member affixed to said valve body member and defining an enclosed air chamber, said second end of said conduit member opening into said enclosed air chamber.

5. A device in accordance with claim 3 wherein said lever arm includes top, bottom, side, and end walls defining an enclosed air chamber, said top wall having an aperture therein, and wherein said visual detection means further comprises:
   a thin-wall conduit member affixed to said top wall and having a first end in fluid communication with said first axial passageway between the cannula and said valve means, and a second end opening into said aperture in said top wall so that said thin-wall conduit member is in fluid communication with said enclosed air chamber.

6. A device in accordance with claim 5 wherein said lever arm is affixed to said valve body member such that in said first position said lever arm is inclined at an angle of 45° with respect to the central axis of said first axial passageway.

7. A device for extracting arterial blood utilizing a cannula or needle comprising:
   (a) a container member under vacuum having a closed end and an open end;
   (b) a valve body member having a first end sized to receive the cannula and the second end affixed to said open end of said container member, said valve body member having a first axial passageway therethrough, said axial passageway including a first portion proximate said first end of said valve body member and a second portion proximate said second end of said valve body member, said first and second portions having first and second inside diameters, respectively, said second inside diameter larger than said first inside diameter;
   (c) a tubular member received within said second portion of said first axial passageway, said tubular member having a continuous side wall of flexible material, said side wall defining a second axial passageway aligned with said first portion of said first axial passageway thereby providing fluid communication between said first portion and said second end of said valve body member;
   (d) means for selectively pinching said side wall of said tubular member upon itself to open and close said second axial passageway, said pinching means normally biased to a first position wherein said second axial passageway is completely closed; and
   (e) means for visual detection of arterial blood pulsations.

8. A device in accordance with claim 7 wherein said valve body member has a recess therein, said recess disposed transverse with respect to said first axial passageway and intersecting with said first axial passageway and wherein said means for selectively pinching said side wall of said tubular member upon itself further comprises:
   (a) a lever arm affixed to said valve body member and mounted for pivotal movement between a first position wherein said second axial passageway is completely closed and a second position wherein said second axial passageway is completely open; and
   (b) a pinching member affixed to said lever arm, said pinching member received for reciprocal movement within said recess in said valve body member, said pinching member having an aperture therein in which said tubular member is received, said lever arm normally biased to said first position wherein said pinching member collapses said side wall of said tubular member upon itself so that said second axial passageway is completely closed.

9. A device in accordance with claim 8 wherein said lever arm has top, bottom, end and side walls defining an enclosed air chamber, said top wall having an aperture therein, and wherein said means for visual detection of arterial blood further comprises:
   (a) a thin-wall conduit member affixed to said top wall of said lever arm and having a first end in fluid communication with said first axial passageway at a point disposed between the cannula and said tubular member, and a second end opening into said aperture in said top wall whereby said thin-wall conduit member is in fluid communication with said enclosed air chamber.

10. A device in accordance with claim 9 further comprising:
    a free floating piston mounted for reciprocal movement within said container member, said free floating piston disposed proximate said open end of said container member prior to extraction of arterial blood.

11. A device in accordance with claim 10 wherein said closed end of said container member has an aperture therein and further comprising:

(a) a removable closure member received within said aperture; and
(b) a plunger means sized to be received within said aperture with said closure member removed, said plunger means adapted to engage said free floating piston for expelling extracted blood from said container member.

* * * * *